United States Patent [19]

Hechenbleikner et al.

[11] 4,113,807
[45] Sep. 12, 1978

[54] ARBUZOV REARRANGEMENT OF TRIPHENYL PHOSPHITE

[75] Inventors: Ingenuin Hechenbleikner, West Cornwall; William Palmer Enlow, Falls Village, both of Conn.

[73] Assignee: Borg-Warner Corporation, Chicago, Ill.

[21] Appl. No.: 795,461

[22] Filed: May 10, 1977

[51] Int. Cl.$^2$ ............................................. C07F 9/40
[52] U.S. Cl. ................................. 260/969; 260/961
[58] Field of Search .................................... 260/969

[56] References Cited

U.S. PATENT DOCUMENTS 3,257,355  6/1966  Bean, Jr. ...................... 260/927 R X

OTHER PUBLICATIONS

Plumb et al, "Chem. Abs.", vol. 58, (1963), 10231g.

Primary Examiner—Anton H. Sutto
Attorney, Agent, or Firm—Joseph Shekleton

[57] ABSTRACT

A process for the preparation of diphenyl phenylphosphonate. The process involves an Arbuzov-type rearrangement of triphenyl phosphite and is characterized by a relatively high reaction temperature.

9 Claims, No Drawings

ARBUZOV REARRANGEMENT OF TRIPHENYL PHOSPHITE

The present invention relates to a novel Arbuzov-type arrangement and, more particularly, it relates to the conversion of triphenyl phosphite to diphenyl phenylphosphonate.

The Michaelis-Arbuzov reaction has long been known. It was first described in J. Russ. Phys. Chem. Soc. 38, 687 (1906). Since then, much work has been done in this field and, as a result of this work, it has come to be accepted that this reaction involves the rearrangement of an organic phosphite with an organic halide, to obtain a phosphonate, as shown in the illustrative equation:

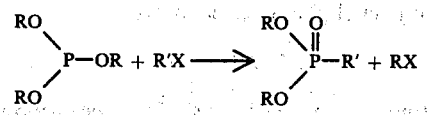

where R and R' are alkyl and X is halogen. A particular type of Michaelis-Arbuzov reaction involves, e.g., a phosphite as above where one of the R groups contains halogen so that the phosphite can undergo an internal rearrangement, as follows:

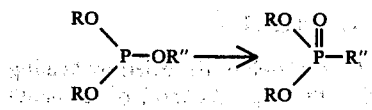

where R" is a haloalkyl group such as 2-chloroethyl or 2-chloropropyl. These types of rearrangements are frequently referred to as Arbuzov rearrangements. Also, if R and R' are identical, only catalytic quantities of R'X are required to cause rearrangement of the phosphite to the phosphonate. On the other hand, when R and R' are different, it will be seen that a stoichiometric amount of R'X is required to prepare the desired phosphonate [R'PO(OR)$_2$] product. In each case the rearrangement is accomplished by heating.

In general, the Arbuzov rearrangements have been limited in their applicability to aliphatic phosphites. In those instances where aromatic phosphites have been found to be susceptible to this reaction, such phosphites have contained at least one aliphatic substituent, e.g., a haloalkoxy or alkoxy group, and it is this aliphatic group which participates in the Michaellis-Arbuzov or Arbuzov rearrangement, as the case may be.

U.S. Pat. No. 2,888,434 (Shashoua) illustrates such rearrangement of tris(2-chloroethyl) phosphite. See column 1, line 50.

U.S. Pat. No. 3,325,563 (Taylor et al.) shows a similar reaction with tris (bromohalopropyl) phosphite. An illustrative equation is as follows:

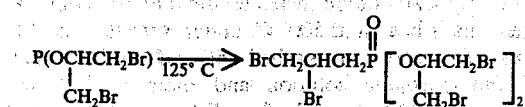

U.S. Pat. No. 3,483,279 (Davis et al.) teaches a process for carrying out the Michaelis-Arbuzov reaction involving passing a thin film of a liquid reaction mixture through a reaction zone at a temperature of 195° to 260° C. Tris(2-bromoethyl) phosphite, diphenyl(2-chloroethyl) phosphite and tris(2-chloroethyl) phosphite are three illustrative starting materials.

U.S. Pat. No. 3,642,960 (Pitt et al.) shows the conversion of a trialkyl phosphite, such as triethyl phosphite, to the corresponding phosphonate; the reaction is carried out at 185° C in an autoclave, using iodine as a catalyst.

U.S. Pat. No. 3,705,214 (Martin) shows the use of an aryl halide such as chlorobenzene in carrying out a Michaelis-Arbuzov reaction. A trivalent phosphorus compound having at least one alkoxy substituent is heated at 100°-250° C with the aryl halide (or it may be a vinyl halide) in the presence of a palladium catalyst. Example II shows the reaction of triethyl phosphite with bromobenzene under these conditions to form diethyl phenylphosphonate.

The reaction of triphenyl phosphite with alkyl and benzyl iodides is shown in 48 C.A. 10538c (1954) and 49 C.A. 9541b (1955). The reaction of trimethyl phosphite with an equimolar quantity of iodobenzene to give a 38% yield of dimethyl phenylphosphonate is shown in 58 C.A. 10231g (1963).

It has now been found that triphenyl phosphite can be converted to diphenyl phenylphosphonate via an Arbuzov-like rearrangement. The process involves preparing a reaction mixture comprising triphenyl phosphite and minor proportions of each of a metal halide catalyst and iodobenzene, and heating said mixture at a temperature above about 200° C.

The degree to which the above conversion is effective can be assessed conveniently by means of gas chromatographic analysis; alternatively, the yield of diphenyl phenylphosphonate can be determined by P$^{31}$NMR spectroscopy. Isolation of the desired product is not an easy matter because, in some instances, a substantial proportion of triphenyl phosphate is formed as a by-product and its separation from the diphenyl phenylphosphonate is difficult.

Relatively high temperatures are required for the reaction. Generally, the temperature is within the range of from about 250° C to about 350° C although in some instances the reaction may be carried out at lower temperatures, e.g., 200° C. The reaction mixture ordinarily is stirred throughout the period of reaction so as to assure uniform heat distribution.

The metal halide catalyst preferably is a Group VIII metal halide. Thus, it may be a halide of iron, cobalt, nickel, palladium, etc. Other metal halides are also contemplated, including those of copper, boron, manganese, zinc, etc. The halide may be a fluoride, chloride, bromide or iodide. Chlorides, bromides and iodides are preferred. Illustrative metal halide catalysts include ferrous chloride, ferrous bromide, nickel iodide, nickel chloride, nickel bromide, cobalt chloride, cobalt bromide, palladium chloride, cupric chloride, cupric iodide, cuprous chloride, cuprous bromide, boron trifluoride, manganous chloride, manganous bromide and zinc chloride. Also contemplated are certain metal complexes of organic phosphites, i.e., those conforming to the structural formula:

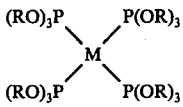

where R is alkyl, aryl, alkaryl or the residue of an aliphatic glycol such as ethylene glycol, pentaerythritol, neopentyl glycol, trimethylene glycol and the like. Illustrative alkyl groups include methyl, ethyl, butyl, hexyl and octyl; the alkyl groups preferably have 1-10 carbon atoms. Illustrative aryl groups include phenyl and naphthyl. Illustrative alkaryl groups include nonylphenyl, dodecylphenyl, diamylphenyl, octylphenyl and the like. The alkyl radicals in the alkaryl groups should contain 5-12 carbon atoms.

M in the above structural formula may be any of the metals which are set out earlier herein as useful in the metal halide catalyst.

The relative proportion of catalyst should be within the range of from about 0.005% to about 1.0% of the amount of triphenyl phosphite. Preferably, this range is from about 0.01% to about 0.2%.

The concentration of iodobenzene should be at least 0.1% based on the weight of triphenyl phosphite. Larger amounts may be used, to increase the yield of diphenyl phenylphosphonate and to shorten the required period of reaction, up to 10%. Still higher concentrations may be used with satisfactory results and are contemplated within the scope of this invention. In lieu of iodobenzene as an added ingredient, iodine itself may be used, because it will react with triphenyl phosphite to form the required iodobenzene. In such instance, as much iodine should be used as needed to produce the above quantity of iodobenzene.

The reaction is carried out simply by heating the triphenyl phosphite, with catalyst and iodobenzene, until the triphenyl phosphite has substantially all been reacted. The progress of the reaction can be monitored by gas chromatographic analysis of samples taken periodically from the reaction mixture. By this means, the triphenyl phosphite content can be ascertained, the absence of which provides a rough estimate of the yield of diphenyl phenylphosphonate. A more precise estimate requires a $P^{31}$NMR analysis of a distilled product so as to sort out a small proportion of triphenyl phosphate which frequently is found in the product mixture, and which is not easily differentiated, as to content, from diphenyl phenylphosphonate by means of gas chromatography. The $P^{31}$NMR analysis shows peaks corresponding to triphenyl phosphite (at $-127.8$, below the signal for phosphoric acid), diphenyl phenylphosphonate (at $-11.6$) and triphenyl phosphate at $+17.7$). No other product seems to be formed in any substantial quantity in the process of this invention. All such analyses may be carried out with a JEOL-FX-60 NMR spectrometer operating at a frequency of 24 $MH_2$($^{31}P$) in the Fourier Transform Mode. Spectra are obtained in $CDCl_3$, using 10 mm. tubes.

EXAMPLE 1

A 1.5-g. sample of cupric chloride is dried by heating to 120° C under reduced pressure. To this dried material there is added 62 g. of triphenyl phosphite and 1.2 g. of iodobenzene and the resulting mixture is heated at 340° C for 5.75 hours. A gas chromatogram shows the disappearance of about 40% of triphenyl phosphite. An additional 3.6 g. of iodobenzene is added to the cooled mixture which then is heated again at 330° C for five hours. The resulting mixture is shown by gas chromatography to comprise only about 20% of triphenyl phosphite.

EXAMPLE 2

A 1.5-g. sample of nickel chloride is dried by heating to 120° C under reduced pressure. To this dried material there is added 62 g. (0.2 mol) of triphenyl phosphite and 1.2 g. of iodobenzene, and the resulting mixture is heated at 320° C, under nitrogen, for 8.5 hours. A gas chromatogram indicates substantially complete disappearance of triphenyl phosphite. The product mixture is distilled to yield a 52.5-g. fraction boiling at 175°-85° C/0.5 mm. This distillate, after seeding and standing overnight at room temperature, crystallizes to a yellow mass of diphenyl phenylphosphonate.

EXAMPLE 3

A mixture of 465 g. (1.5 mols) of triphenyl phosphite, 9.1 g. of iodobenzene and 2 g. of nickel iodide (dried by heating to 120° C) are heated at 250° C, under nitrogen, for 26.5 hours. An additional 1.5 g. of nickel iodide is added after 10.5 hours. Gas chromatographic analysis shows the disappearance of triphenyl phosphite to be about 90% complete.

EXAMPLE 4

A 1.5-g. sample of ferrous chloride, dried by heating to 120° C, is mixed with 62 g. (0.2 mol) of triphenyl phosphite and 1.2 g. of iodobenzene, and the resulting mixture is heated at 300°-320° C, under nitrogen, for 4.5 hours. Gas chromatographic analysis shows the disappearance of about 15% of the triphenyl phosphite.

EXAMPLE 5

A mixture of 155 g. (0.5 mol) of triphenyl phosphite, 0.5 g. of tetrakis(phenylneophenyl phosphite) nickel, and 30 g. of iodobenzene is heated at 200° C, under nitrogen, for 9.5 hours, then distilled. The distillate boils over a range of 160°-194° C/0.1 mm. and is collected in four fractions as follows:

| | |
|---|---|
| 1. to 160° C/0.1 mm. | 30.0 g. |
| 2. 160° C/0.1 mm. | 36.0 g. |
| 3. 180° C/0.1 mm. | 44.0 g. |
| 4. 186-194° C/0.1 mm. | 52.5 g. |

Fractions Nos. 3 and 4 are subjected to $P^{31}$NMR analyses with the following results:

| | $(C_6H_5O)_3P$ | $(C_6H_5O)_3PO$ | $C_6H_5PO(OC_6H_5)_2$ |
|---|---|---|---|
| 3. | 86% | 8% | 6% |
| 4. | 59% | 23% | 18% |

EXAMPLE 6

A mixture of 232.5 g. (0.75 mol) of triphenyl phosphite, 2.3 g. of nickel iodide (dried as above) and 4.5 g. of iodobenzene is heated at 300° C, under nitrogen, for eight hours. The mixture is washed with a dilute aqueous sodium hydroxide solution and then distilled. $P^{31}$NMR analyses, before and after distillation, show the following:

|  | $(C_6H_5O)_3P$ | $(C_6H_5O)_3PO$ | $C_6H_5PO(OC_6H_5)_2$ |
| --- | --- | --- | --- |
| Before Distillation | 4% | 24% | 69% |
| After Distillation | 7% | 26% | 67% |

All parts and percentages herein, unless otherwise expressly stated, are by weight.

We claim:

1. A process for the preparation of diphenyl phenylphosphonate comprising preparing a reaction mixture comprising triphenyl phosphite and minor proportions of each of a metal halide or metal phosphite complex catalyst, and iodobenzene, and heating said mixture at a temperature above about 200° C.

2. The process of claim 1 wherein the metal halide catalyst is a Group VIII metal halide.

3. The process of claim 1 wherein the metal halide catalyst is a copper halide.

4. The process of claim 1 wherein the metal halide catalyst is a nickel halide.

5. The process of claim 1 wherein the metal halide catalyst is nickel bromide.

6. The process of claim 1 wherein the metal halide catalyst is cobalt chloride.

7. The process of claim 1 wherein the metal halide catalyst is copper chloride.

8. The process of claim 1 wherein the amount of iodobenzene present in the reaction mixture is from about 0.1% to about 10% of the amount of triphenyl phosphite.

9. The process of claim 1 wherein the amount of metal halide catalyst present in the reaction mixture is from about 0.005% to about 1.0% of the amount of triphenyl phosphite.

* * * * *